United States Patent
Davis

(10) Patent No.: US 8,431,075 B2
(45) Date of Patent: *Apr. 30, 2013

(54) MOBILE UV STERILIZATION UNIT FOR FIELDS AND METHOD THEREOF

(75) Inventor: Michael E. Davis, Indianapolis, IN (US)

(73) Assignee: GreenZapr, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/590,220

(22) Filed: Aug. 21, 2012

(65) Prior Publication Data

US 2012/0315186 A1 Dec. 13, 2012

Related U.S. Application Data

(62) Division of application No. 12/775,515, filed on May 7, 2010.

(51) Int. Cl.
*A61L 2/00* (2006.01)

(52) U.S. Cl.
USPC .......................................................... 422/24

(58) Field of Classification Search ............... 422/24; 588/309

See application file for complete search history.

(56) References Cited

U.S. PATENT DOCUMENTS

| 3,633,679 | A | 1/1972 | Dahlberg et al. | |
|---|---|---|---|---|
| 3,846,932 | A * | 11/1974 | Bialobrzeski | 43/138 |
| 5,902,552 | A | 5/1999 | Brickley | |
| 5,968,455 | A | 10/1999 | Brickley | |
| 7,459,694 | B2 | 12/2008 | Scheir et al. | |
| 8,258,202 | B2 * | 9/2012 | Chasser et al. | 523/122 |
| 2002/0139355 | A1 | 10/2002 | Gracyalny et al. | |
| 2003/0159840 | A1 | 8/2003 | Schmidt | |
| 2004/0244138 | A1 * | 12/2004 | Taylor et al. | 15/319 |
| 2008/0295271 | A1 | 12/2008 | Perunicic | |
| 2010/0104471 | A1 | 4/2010 | Harmon et al. | |

FOREIGN PATENT DOCUMENTS

| JP | 09239352 A | 9/1997 |
|---|---|---|
| KR | 20-0170293 | 2/2000 |
| KR | 20-0353596 | 6/2004 |
| KR | 20-03080226 | 3/2005 |
| KR | 10-0518620 | 10/2005 |
| KR | 20-0407560 | 1/2006 |

* cited by examiner

*Primary Examiner* — Kevin Joyner
(74) *Attorney, Agent, or Firm* — Woodard, Emhardt, Moriarty, McNett & Henry LLP

(57) ABSTRACT

A mobile ultraviolet sterilization vehicle. A plurality of UV lamps are removably mounted to a wheeled vehicle. A plurality of tines and a brush are mounted to the vehicle extending across the width thereof and into the supporting surface to position the supporting surface to receive the UV light.

10 Claims, 5 Drawing Sheets

MOBILE UV STERILIZATION UNIT FOR FIELDS AND METHOD THEREOF

REFERENCE TO RELATED APPLICATION

This application is a divisional of U.S. patent application Ser. No. 12/775,515, filed May 7, 2010, which is hereby incorporated by reference.

BACKGROUND OF THE INVENTION

1. Field of the Invention

The present invention is in the field of apparatus for sterilizing fields and more specifically sports fields.

2. Description of the Prior Art

High-performance, artificial athletic fields are increasingly being installed and used in communities. Many of these fields are "infill turf systems" in which blades of synthetic grass are tucked into a backing system that is covered with a deep layer of sand and/or synthetic particles (the infill material). The infill materials are often made of small particles of rubber or plastic, which fills the spaces between the fibers (blades of "grass") to hold the fibers up and to provide a cushion surface.

The infill material and synthetic fibers can provide a host for a variety of substances including mold, bacteria and a variety of germicidal agents. The current procedure is to spray various chemicals on the field to thereby sterilize the field and provide a safe environment. Spraying of chemicals onto artificial fields is quite expensive due not only to the labor involved but also the cost of raw materials.

An alternate approach in decontaminating surfaces is through the use of ultraviolet light. For example, In U.S. Pat. No. 7,459,694, there is disclosed a mobile germicidal system for decontaminating walls and a ceiling of a room. Germicidal lamps are positioned adjacent the wall and/or ceiling to thereby sterilize the surface. U.S. Pat. No. 5,902,552 discloses an ultraviolet air sterilization device for connection to an air handling duct for the purpose of sterilizing the air as it flows through the duct. U.S. Pat. No. 5,968,455 discloses a mobile unit incorporating many of the features of U.S. Pat. No. 5,902,552 and includes a wheeled carnage with a handle to allow the operator to traverse the sterilization device over a floor covering.

Despite the prior devices and the availability of germicidal lamps and associated fixtures, there is still a need for a mobile device that is easily movable across a field such as a synthetic soccer or football field for quickly destroying undesirable agents existing on the synthetic field. Further, since the synthetic fibers have embedded therebetween loose infield material, simply passing a UV light over the field may not maximize the sterilization. Thus, there is a further need to have on the vehicle infill material devices for moving and turning over the infill material thereby exposing the infill material to the sterilization lamps.

The so called "green effect" is the characteristic of a machine, method, etc. to achieve a desired result with the least impact on the environment. There is a need to have an aforementioned mobile UV sterilization apparatus that is battery powered that is rechargeable once the energy is depleted. Disclosed herein is an apparatus and method which fulfills all of the aforementioned needs.

SUMMARY OF THE INVENTION

One embodiment of the present invention is a method of destroying infectious material present on a field having blades and comprising the steps of moving a wheeled vehicle across a field, engaging the blades on the field by the vehicle as the vehicle is moved across the field, carrying a source of ultraviolet light on the vehicle, shining the source of ultraviolet light downwardly against the blades to destroy infectious material on the field, carrying a source of electrical energy on the vehicle, and powering the ultraviolet light with the electrical energy.

Another embodiment of the present invention is a vehicle to move across a sports field having blades to destroy infectious material on the field comprising a frame, a wheel rotatably mounted on the frame and extending downwardly to support the frame, a source of ultraviolet light mounted on the frame and having ultraviolet lamps to shine downwardly against the field, a source of electrical energy mounted on the frame and connected to the ultraviolet lamps and an engager mounted on the frame forwardly of the source of ultraviolet light that extends down contacting and positioning the blades on the field to receive the ultraviolet light.

It is an object of the present invention to provide a new method and apparatus for sterilizing sports fields.

A further object of the present invention is to provide a mobile ultraviolet sterilization vehicle that will maximize the sterilization of a sports field.

Yet a further object of the present invention is to provide an ultraviolet sterilization vehicle designed to have minimum impact on the environment.

Related objects and advantages of the present invention will be apparent from the following description.

DESCRIPTION OF THE PREFERRED EMBODIMENT

Figure 1:
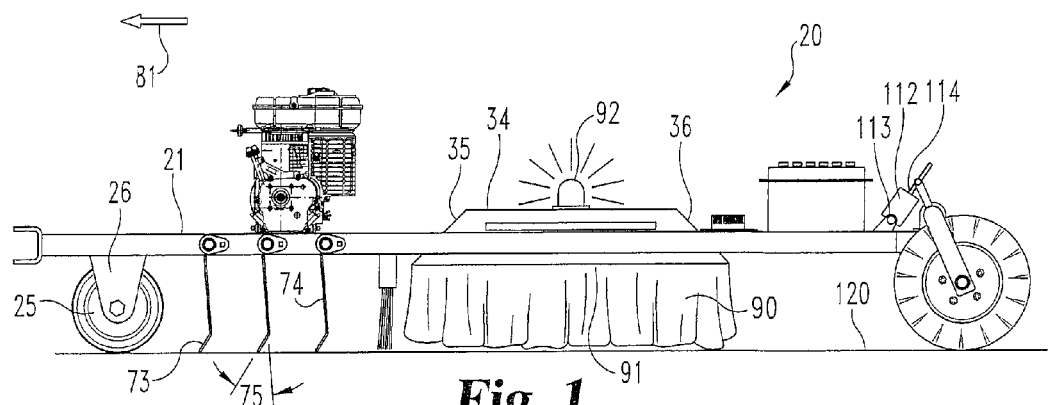
FIG. 1 is side view of the mobile vehicle incorporating the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
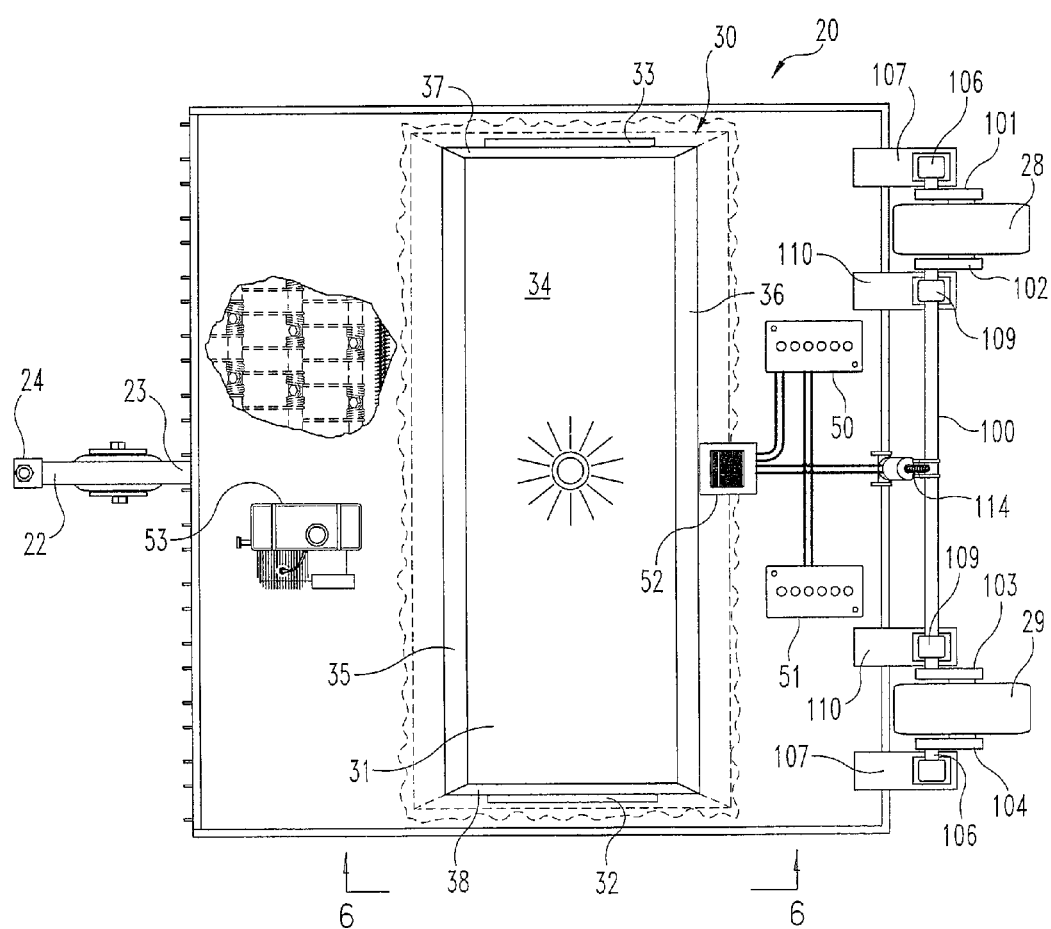
FIG. 2 is a fragmentary top view of the vehicle of FIG. 1.
Figure 3:
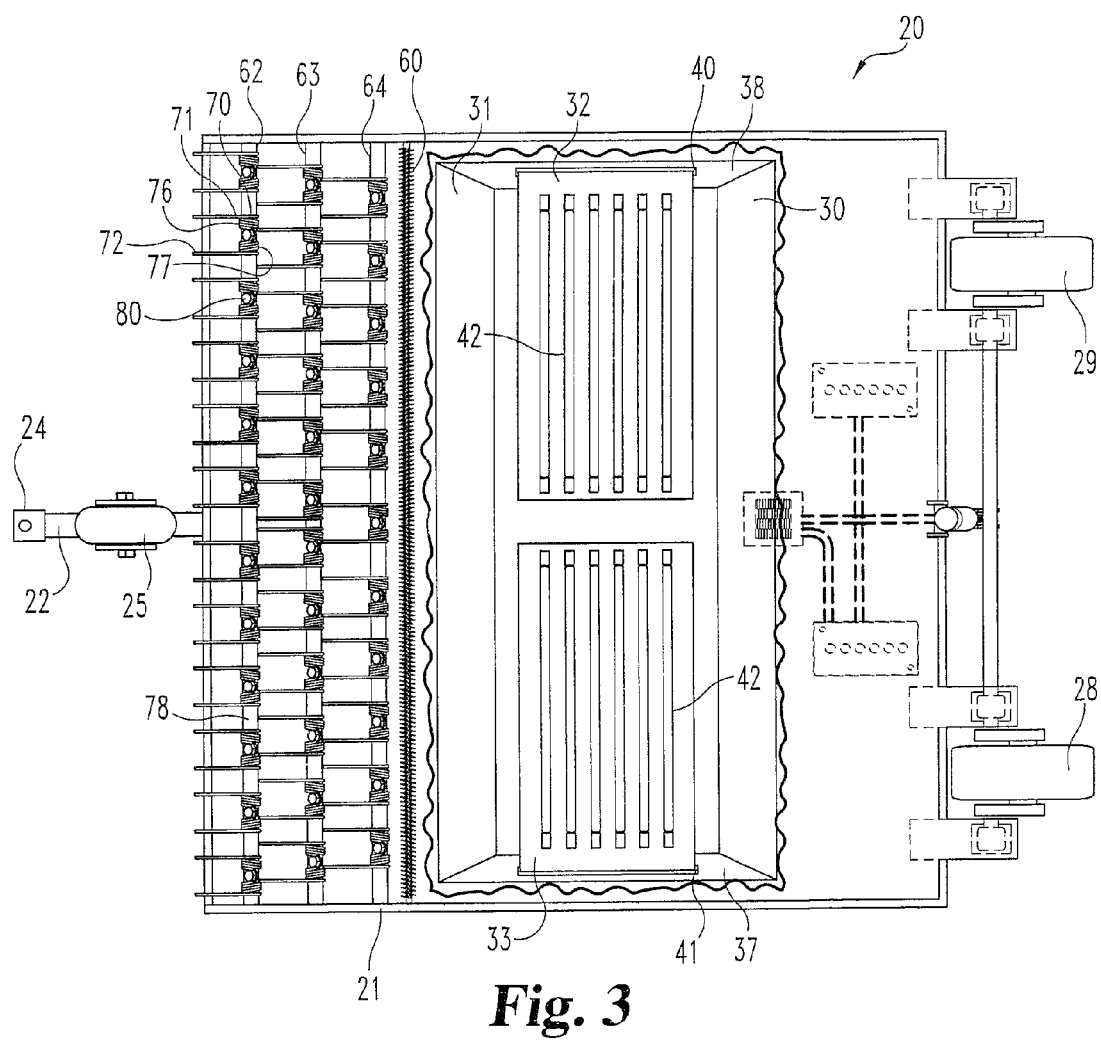
FIG. 3 is a bottom view of the vehicle of FIG. 1.

Referring now more particularly to FIGS. 1-3, there is shown a mobile vehicle 20 having a main frame 21 with a general rectangular configuration. A tow bar 22 has a proximal end 23 fixedly mounted to frame 21 and a distal end 24 forming a conventional hinge that can be coupled to a towing vehicle, such as a cart or tractor. Wheel 25 is rotatably mounted to a pair of flanges 26 fixedly mounted to bar 22 and depends therefrom allowing wheel 25 to engage the ground 120 and support frame 21. At the opposite end of the frame, a pair of wheels 28 and 29 is rotatably mounted to frame 21. Wheels 25, 28 and 29 support the vehicle as the vehicle is towed across a field.

A source of ultraviolet light 30 is mounted to frame 21 has a plurality of ultraviolet lamps to shine downwardly against the field. The source of ultraviolet light 30 has a housing 31 closed on the top but opened on the bottom to allow the light from the ultraviolet lamps mounted therein to shine downwardly. Housing 31 has a top wall 34 joined to a pair of side walls 35 and 36 extending across the width of the vehicle and joined to a pair of end walls 37 and 38. Walls 35-38 extend angularly downward from the top wall and are fixed to frame 21.

A pair of identical ultraviolet lamp fixtures 32 and 33 is slidably mounted to housing 31 from the opposite sides thereof. End wall 38 has a slot 40 into which lamp fixture 32 is slidable. Likewise, end wall 37 is provided with a slot 41 through which lamp fixture 33 is slidable. Both lamp fixtures 32 and 33 rest atop shelves (not shown) provided within housing 31 to support the fixtures. Each lamp fixture 32 and 33 includes six removable ultraviolet lamps that are removably mounted thereto. The ultraviolet lamps 42 (FIG. 3) are arranged in rows extending lengthwise across the width of the vehicle. In the embodiment shown in FIG. 3, a total of 12 lamps are shown with six parallel lamps extending from one side of the vehicle to the approximate middle of the vehicle whereas the second set of parallel lamps 42 extend from the general middle location of the vehicle to the opposite side of the vehicle. Ultraviolet lamps are commercially available from a variety of lamp manufactures. Conventional male and mating female electrical connectors are provided in housing 31 to connect lamp fixtures 32 and 33 and thus lamps 42 to a source of electrical energy carried on the vehicle. The connectors are automatically electrically connected together by the action of fixtures 32 and 33 being slid into position.

A pair of identical 12 volt, 150 watt DC gel cell batteries 50 and 51 is mounted atop frame 21 and is connected via a conventional inverter 52 to lamps 42. The lamps operate on 115 volt AC with inverter 52 converting the DC power to AC power to energize the lamps.

A conventional generator and engine 53, is mounted atop frame 21 and is connected via inverter 52 to recharge batteries 50 and 51. In addition, inverter 52 may be connected by an auxiliary cord to a stationary source of alternating current, such as available in a building to recharge the batteries when not in use whereas engine 53 may be used to recharge the batteries both when the batteries are in use and not in use.

A brush 60 (FIG. 3) extends across the width of the vehicle and is attached and mounted to frame 21. Brush 60 includes a plurality of downwardly extending bristles to engage the synthetic field fibers to cause the fibers to extend generally vertical allowing the ultraviolet lamps to shine downwardly through the open bottom of housing 31 onto both sides of the synthetic fibers.

Three rows 62, 63 and 64 of downwardly extending tines are aligned to be parallel to each other and extend across the width of the vehicle and are mounted to frame 21. The tines are provided to contact the infill material between the synthetic upstanding fibers to move and turn over the infill material thereby exposing the material to the ultraviolet light. Brush 60 is positioned between the most rearward row 64 of tines and the source of ultraviolet light 30. The brush form is an engager that contacts the synthetic blades prior to the ultraviolet lamps shining thereon. The brush therefore positions the blades on the field to receive the ultraviolet light and destroy any infectious material thereon.

Figure 4:
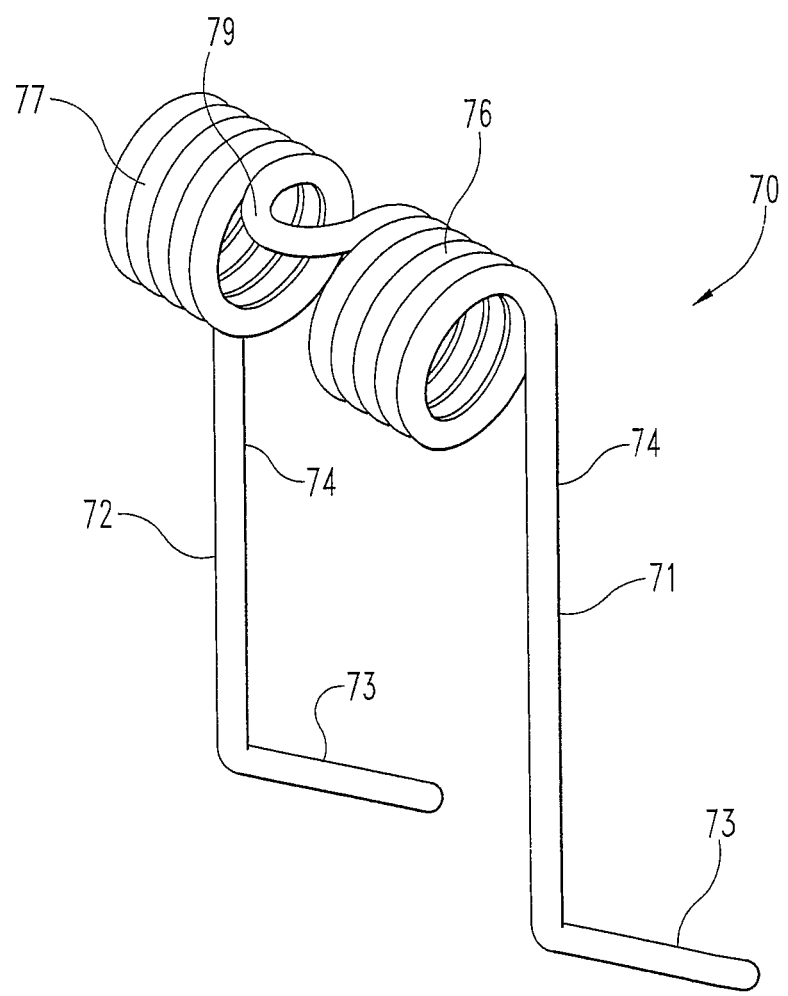
FIG. 4 is an enlarged perspective view of a pair of the tines for mounting to one of the rows of tines.
Figure 5:
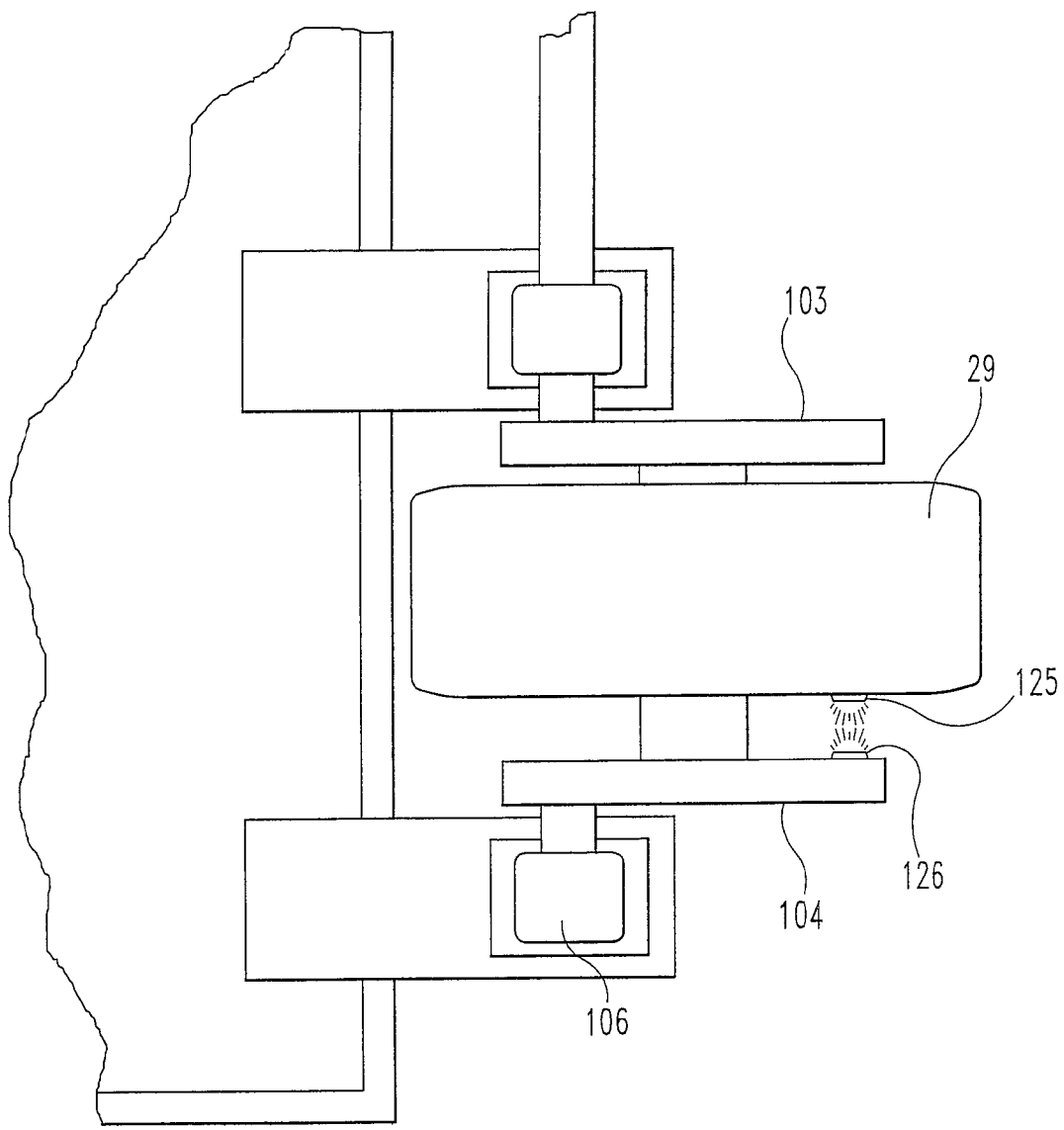
FIG. 5 is an enlarged fragmentary view of rear wheel 29 illustrating the positioning of the infrared sensor to detect stationary movements.
Figure 6:
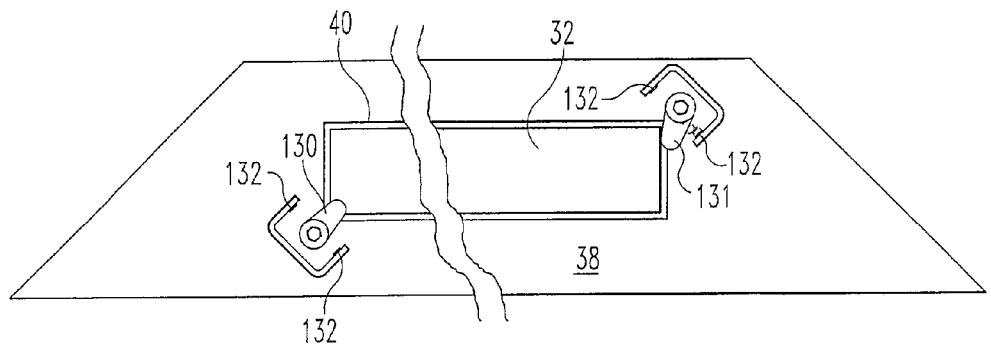
FIG. 6 is an enlarged fragmentary side view looking in the direction of arrows 6-6 of FIG. 2 of light fixture 32 held in place by a pair of cam locks.

Row 62 of tines will now be described it being understood that an identical description applies to tine rows 63 and 64. The tines are grouped in pairs. For example, pair 70 (FIGS. 3 and 4) includes a pair of wire shaped downwardly extending members 71 and 72 having bottom end portions 73 integrally joined to upwardly extending straight portions 74 with the proximal ends 73 (FIG. 1) arranged with respect to straight portions 74 at an approximate angle 75 of 40 degrees. The top end of straight portion 74 of tine 71 is integrally attached to a helically wound portion 76, in turn, integrally joined to a second helically wound portion 77, in turn, integrally joined to the top end of straight portion 74 of tine 72. Tines 71 and 72 are identical in construction.

Helical portions 76 and 77 are mounted to rod 78 (FIG. 1) that extends therethrough. Helical portion 76 and 79 are integrally joined together by a c-shaped middle section 79 (FIG. 4) that rests against a protruding head 80 (FIG. 1) extending outwardly from and fixedly mounted to rod 78. Head 80 extends into c-shaped section 79 thereby limiting movement of tines 71 and 72. As the vehicle moves in a forward direction 81 (FIG. 1), bottom ends 73 of each tine 71 and 72 contact the infill material between the upstanding synthetic fibers causing tines 71 and 72 to pivot backward towards the rear of the vehicle; however, c-shaped portion 79 in conjunction with the helical spring portion 76 and 77 return the tines to their original positions.

A flexible skirt 90 has a top end 91 mounted to frame 21 with the skirt extending down immediately above the field to prevent the ultraviolet light shining outward to an observer standing adjacent the vehicle. An LED light 92 is mounted to the top wall 34 of housing 31 to shine and provide a warning that the ultraviolet lamps are emitting ultraviolet light.

Wheels 28 and 29 are rotatably mounted to a pair of flanges, in turn, mounted to rod 100 that may be rotated to pivot the wheels up and down. For example, a pair of downwardly extending flanges 101 and 102 rotatably receive wheel 28 whereas downwardly extending flanges 103 and 104 rotatably receive wheel 29. The outward facing flanges 101 and 104 are mounted to bearings 106, in turn, fixedly mounted to flanges 107 affixed to frame 21. Rod 100 is rotatably received by bearings 109 mounted atop flanges 110 fixedly mounted to the frame. An actuator 112 (FIG. 1) has a bottom end 113 pivotally mounted to frame 21 and has an extendable rod 114 attached to rod 100 being operable to rotate rod 100. Rod 100 is located off center with respect to the rotational axis of wheels 28 and 29 with the result that rotation of rod 100 causes wheels 28 and 29 to pivot upwardly or downwardly with respect to the supporting surface 120 upon which the vehicle rides.

In operation, when moving the vehicle across supporting surface 120, when it is desired that the tines not contact the supporting surface, rod 114 is extended causing wheels 28 and 29 to pivot and move downwardly thereby lifting frame 21 to the point that the tines do not contact the supporting surface. In the event it is desired that the tines contact supporting surface 120, then rod 114 is retracted causing upward movement of wheels 28 and 29 thereby lowering frame 21 and allowing the bottom portions 73 of the tines to contact supporting surface 120.

The method of destroying the infectious material present on a field having synthetic upstanding blades includes the step of moving a wheeled vehicle across the field while engaging the blades on the field by the vehicle. A source of ultraviolet light is carried on the vehicle and is positioned to shine the source of ultraviolet light downwardly against the blades to destroy the infectious material. The method includes the additional step of carrying a source of electrical energy on the vehicle to power the ultraviolet light. The engaging step includes the sub-step of brushing the blades to position the blades to receive the ultraviolet light thereby destroying the infectious material. Further, the method includes the additional step of shielding the ultraviolet light to provide safety for an operator of the vehicle by minimizing the visibility of the ultraviolet light from aside the vehicle. The method further includes the step of contacting the loose material between the blades by the vehicle as vehicle is moved across the field to expose the loose material to the ultraviolet light shining downwardly thereon. The step of contacting the loose material includes a sub-step of extending rigid members down from the vehicle and between the blades to move and turn over the loose material. In order to adjust the bottom ends of the tines relative to the field supporting surface, the method includes adjustably raising and lowering the vehicle by a pair of wheels located on the rear of the vehicle to controllably limit contact with the field. In the event the bottom ends of the tines are to be positioned apart form the supporting surface, then the rear wheels are moved downwardly sufficient so as to raise the vehicle frame and position the bottom ends of the tines apart from the supporting surface. On the other hand, if it is desired to control the amount of penetration of the tines into the loose material on the field, then the wheels are raised until the bottom ends of the tines penetrate the desired amount into the loose material. In order to maintain the ultraviolet lamps on the vehicle, the lamps are removably held to allow replacement thereof.

End walls 37 and 38 and side walls 35 and 36 of housing 31 as well as the top wall 34 of the housing provide inner surfaces to reflect the ultraviolet light downwardly. The slanted walls 35-38 are arranged at an angle to allow the ultraviolet light to extend beyond the immediate outline of each lamp.

In certain instances, it is desired to control the amount of ultraviolet light that shines upon the synthetic blades. That is, in the event the vehicle is stationary for a specified duration, then it is desirable to turn off the ultraviolet lamps to prevent the ultraviolet light from shining upon the synthetic blades for an unacceptable duration. To this extent, a commercially available infrared sensor 126 is mounted to flange 104 and is operable to detect movement of target 125 mounted to the mutually facing surface of wheel 29. A timing circuit is provided so that once rotation of wheel 29 stops for a predetermined time, for example 30 seconds, sensor 126 sends a signal to inverter 52 interrupting the flow of electrical energy to the ultraviolet lamps thereby turning the lamps off. As a result, the method disclosed herein includes deactivating the source of ultraviolet light when the vehicle is stationary on the field for a preset time.

In the event light fixtures 32 and 33 become accidentally dislodged from housing 31, micro switches are activated by cam locks normally holding the light fixtures in place to interrupt the flow of electrical energy to the light fixtures. For example, a pair of cam locks 130 and 131 is eccentrically mounted to end wall 38 and are designed to extend inwardly over the corners of light fixture 32. In the event the cam locks rotate allowing the light fixture 32 to move outwardly, then the cam locks contact conventional micro switches 132, in turn, connected to inverter 52 interrupting the flow of electrical energy to light fixtures and ultraviolet lamps. Cam locks identical to locks 130 and 131 along with switches identical to switches 133 are provided on wall 33 to hold fixture 33 and control the flow of electrical energy to fixture 33.

Some synthetic fields do not have crumb rubber (infill material) between the synthetic blade fibers. Thus, the main body of the supporting rod for each row of tines 62-64 may be rotated to rotate the tines upwardly apart from the field. For example, the ultraviolet lamp on the vehicle may be used to kill fungus on the blades of a standard golf green; however, it is imperative that the tines not extend down and engage the dirt between the non-synthetic blades of grass.

Figure 7:
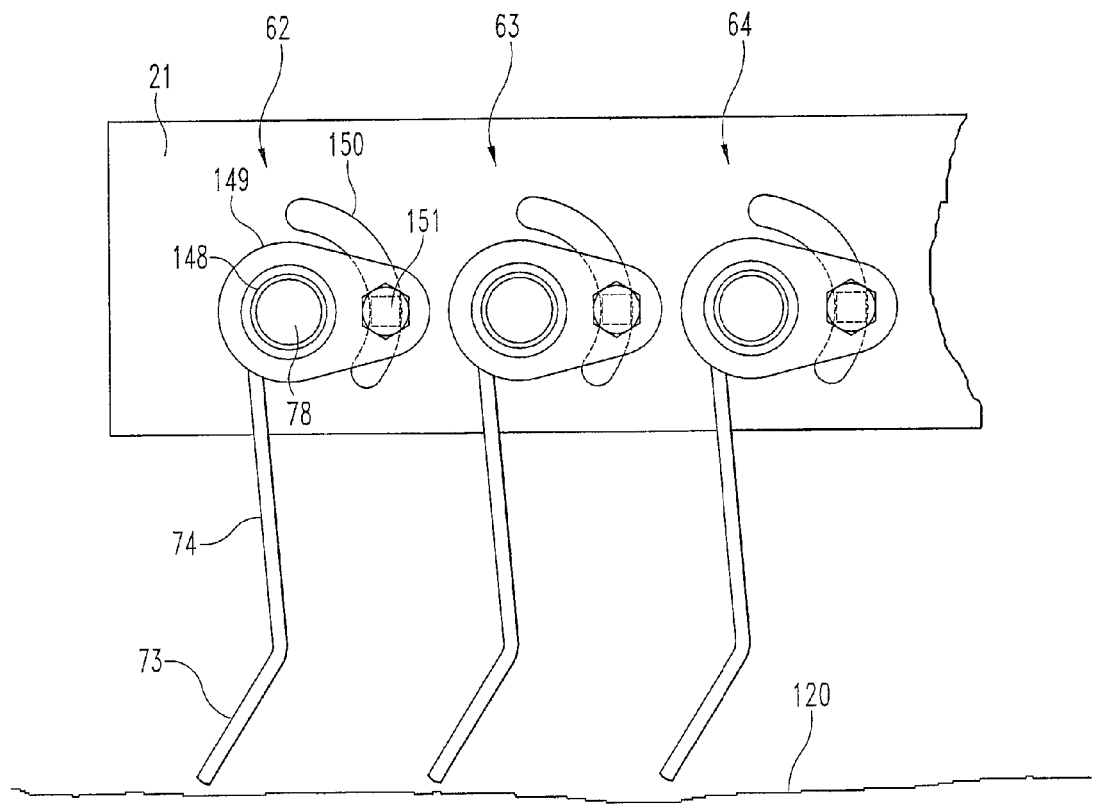
FIG. 7 is an enlarged fragmentary side view of frame 21 illustrating the mounting arrangement of the rows of tines.

Each row of tines 62-64 (FIG. 3) includes a rod rotatably mounted at its opposite ends to the side walls of main frame 21 or interior walls, in turn, mounted to frame 21. Each rod includes a flange integrally secured thereto at each opposite end of the rod. The flange has a teardrop shape with the flange mounted eccentrically with respect to the rod. For example, rod 78 includes an end 148 (FIG. 7) integrally attached to one end of teardrop shape flange 149 positioned against the side wall of frame 21. The opposite end of flange 149 includes a slot 150 through which fastener 151 extends. Flange 149 can be pivoted about the longitudinal axis of rod 78 with fastener 151 moving between the opposite extremes of slot 150 to position the bottom ends 73 of the tines apart from supporting surface 120 or position the tips of bottom tine ends 73 into the supporting surface at a controlled distance.

Many variations are contemplated and included in the present invention. For example, the embodiment shown in the drawing has a single brush extending across the width of the vehicle between the tines and the UV lamps. It is also possible to position a separate brush between rows 62 and 63 and another brush between rows 63 and 64 in order to increase the repositioning of the synthetic turf fibers and infill material therebetween.

Another variation of the present invention includes adding standard louvers to housing 31 in order to allow heat within the housing and generated by the UV lamps to escape upwardly. The UV lamps may take many different configurations. In the embodiment shown in the drawing, each lamp fixture 32 and 33 is approximately 36 inches wide by 36 inches in length and 6 inches in height. Each lamp fixture is shown as having six UV lamps removably mounted thereto; however, it is to be understood that at the present invention includes more than or less than two light fixtures and more than or less than six UV lamps for each lamp fixture.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of destroying infectious material present on a field having synthetic blades with opposite sides and loose material between the blades comprising the steps of:

moving a wheeled vehicle across a field, said vehicle having a brush with bristles, a downwardly extending wire shaped member, and an ultraviolet light;

contacting blades on the field as said vehicle is moved across the field to move the blades and including the sub-step of brushing with bristles of a brush said blades to position said blades to extend generally vertically to receive ultraviolet light on both sides of the blades destroying infectious material thereon;

downwardly extending said member to contact and penetrate into said loose material turning over loose material between said blades as said vehicle is moved across the field to expose the loose material to ultraviolet light shining down from the vehicle destroying infectious material on said loose material;

shining said ultraviolet light downwardly against the blades and said loose material to destroy infectious material located on the synthetic blades and loose material;

carrying a source of electrical energy on said vehicle; and, powering the ultraviolet light with said electrical energy.

2. The method of claim 1 comprising the additional step of:

shielding said ultraviolet light to provide safety for an operator of said vehicle by minimizing the visibility of said ultraviolet light from aside said vehicle.

3. The method of claim 1 and comprising the additional step of:

adjustably moving said downwardly extending member relative to the loose material to control the amount of penetration of said member into said loose material.

4. The method of claim 1 and comprising the additional step of:

removably holding said ultraviolet light on said vehicle to allow replacement thereof.

5. The method of claim 1 and comprising the additional step of:

reflecting said ultraviolet light downwardly against said blades and said loose material.

6. A method of destroying infectious material present on a field having synthetic blades with opposite sides and material between the blades comprising the steps of:

moving a wheeled vehicle across a field, said vehicle having a brush, and an ultraviolet light;

contacting synthetic blades on the field as said vehicle is moved across the field to move the blades by brushing with a brush said blades to position said blades to extend upwardly to receive ultraviolet light destroying infectious material thereon;

shining said ultraviolet light downwardly against the blades and said material between the blades to destroy infectious material located on the blades and material;

carrying a source of electrical energy on said vehicle; and, powering the ultraviolet light with said electrical energy.

7. The method of claim 6 and comprising the additional step of:

brushing the blades with said brush to position said blades to receive ultraviolet light on both sides of the blades destroying infectious material thereon.

8. The method of claim 7 and comprising the additional step of:

shining ultraviolet light onto said material between said blades to destroy infectious material on said material between the blades.

9. A method of destroying infectious material present on a field having synthetic blades with opposite sides and loose material between the blades comprising the steps of:

moving a wheeled vehicle across a field, said vehicle having a brush, a downwardly extending wire shaped member, and an ultraviolet light;

contacting blades on the field by said vehicle as said vehicle is moved across the field to move the blades and including the sub-step of brushing with a brush said blades to position said blades to extend generally vertically to receive ultraviolet light on both sides of the blades destroying infectious material thereon;

downwardly extending said wire shaped member to contact and penetrate into loose material moving the loose material between said blades as said vehicle is moved across the field to expose the loose material to ultraviolet light shining down from the vehicle destroying infectious material on the loose material; and, shining said ultraviolet light downwardly against the blades and the loose material to destroy infectious material located on the blades and loose material.

10. A method of destroying infectious material present on a field having synthetic blades with opposite sides and material between the blades comprising the steps of:

moving a wheeled vehicle across a field, said vehicle having a brush, a downwardly extending wire shaped member, and an ultraviolet light;

contacting blades on the field by said vehicle as said vehicle is moved across the field to move the blades and including the sub-step of brushing with a brush said blades to position said blades to extend generally vertically to receive ultraviolet light on opposite sides of the blades destroying infectious material thereon;

holding said wire shaped member in spaced relationship from said material between said blades unless the material between the blades is in a loose condition relative to said blades and then contacting said material in a loose condition with said wire shaped member by downwardly extending said wire shaped member to contact and penetrate into said material in a loose condition overturning same as said vehicle is moved across the field to expose the material overturned to ultraviolet light shining down from the vehicle destroying infectious material thereon; and, shining said ultraviolet light downwardly against the blades and said material between the blades to destroy infectious material located thereon and on the blades.

* * * * *